United States Patent [19]

Sterk et al.

[11] Patent Number: 5,010,095

[45] Date of Patent: Apr. 23, 1991

[54] N-(W-SUBSTITUTED ALKYL)-N'-(IMIDAZOL-4-YL)ALKYL) GUANIDINE

[75] Inventors: Geert J. Sterk, RN Utrecht; Henk Timmerman, VM Voorschoten; Henk van der Goot, GW Hoofddorp, all of Netherlands

[73] Assignee: Cedona Pharmaceuticals B.V., Haarlem, Netherlands

[21] Appl. No.: 297,549

[22] PCT Filed: Jun. 19, 1987

[86] PCT No.: PCT/NL87/00013

§ 371 Date: Nov. 23, 1988

§ 102(e) Date: Nov. 23, 1988

[87] PCT Pub. No.: WO87/07891

PCT Pub. Date: Dec. 30, 1987

[30] Foreign Application Priority Data

Jun. 19, 1986 [NL] Netherlands .................. 8601585

[51] Int. Cl.$^5$ .............................. C07D 233/64
[52] U.S. Cl. ...................... 514/400; 548/342; 548/343
[58] Field of Search ............. 548/342, 343; 514/400

[56] References Cited

U.S. PATENT DOCUMENTS

| | | | |
|---|---|---|---|
| 4,013,659 | 3/1977 | Durant et al. | 424/263 |
| 4,098,898 | 7/1978 | Durant et al. | 548/342 X |
| 4,166,860 | 9/1979 | Douglas et al. | 424/273 |
| 4,192,879 | 3/1980 | Durant et al. | 548/342 X |

FOREIGN PATENT DOCUMENTS

| | | |
|---|---|---|
| 3512084 | 4/1985 | Fed. Rep. of Germany . |
| 3528214 | 8/1985 | Fed. Rep. of Germany . |
| 3528215 | 8/1985 | Fed. Rep. of Germany . |

OTHER PUBLICATIONS

Sterk, et al., "Histaminergic Compounds", Eur. J. Med. Che., 22 (6), 491–8, 1987.

*Primary Examiner*—Mary C. Lee
*Assistant Examiner*—Catherine Scalzo
*Attorney, Agent, or Firm*—Burgess, Ryan and Wayne

[57] ABSTRACT

N-(2-substituted alkyl)-N'[(imidazole-4-yl)alkylguanidines are provided by the reaction of a primary amine with benzoylisothiocyante to a benzoylthiourea derivative, followed by hydrolysis of this derivative to form the corresponding thiourea, converting this thiourea with methyliodide into an isothiourea and producing the desired compound by reaction of the isothiourea with aminopropylimidazole or aminoethylimidazole. The compound can be converted into an acid addition salt or the free compound obtained from such salt. The compounds are useful as the active ingredient in pharmaceutical compositions for the treatment of congestion, heart failure and some allergic conditions.

9 Claims, No Drawings

N-(W-SUBSTITUTED ALKYL)-N'-(IMIDAZOL-4-YL)ALKYL) GUANIDINE

The invention relates to a N-(ω-substituted alkyl)-N'-[(imidazol-4-yl)alkyl]guanidine.

Impromidine, or N-[2-(5-methylimidazol-4-yl methylthio)ethyl]-N'-[3-(imidazol-4-yl)propyl]guanidine is known as a specific and the most potent histamine $H_2$-agonist, Dependent on the used test system it either behaves like a partial or like a complete agonist having a potency of 5–800 times that of histamine (Proc. VIIIth Internat. Symp. Med. Chem. Uppsala, pages 202–203 (1985) Eds R. Dahlbom and J. L. G. Nilsson). Because of its effect on the release of histamine from mast cells, there might be some use of impromidine in the treatment of allergic conditions. However, a major drawback for the clinical use of impromidine is its relatively high potency in stimulating the gastric acid secretion and its effect on vasoconstriction and vasodilation.

Now a series of new impromidine-related compounds was discovered, said compounds having a high histamine $H_2$-agonistic acitivity on the guinea-pig right atrium with a relatively low activity on the guinea-pig gastric acid secretion and a potent histamine $H_1$-antagonism as tested on both the guinea-pig ileum and the guinea-pig trachea. Because of this combination of histamine $H_1$-antagonism and $H_2$-agonism in one compound, these compounds are of clinical significance for e.g. the treatment of congestive heart failures and some allergic conditions.

These new compounds are N-(ω-substituted alkyl)-N'-[imidazol-4-yl)alkyl]guanidines of formula 1, wherein:
m is 1, 2 or 3;
n is 2 or 3;
X is S, O or $CH_2$, and
Y is a R substituted diphenylmethyl group or (10,11-dihydro) 5H-dibenzo-[a-d]-cyclohepten-5-yl group, or is (b)

wherein
$Y_1$ is a R-substituted phenyl group and
Y is also a R-substituted phenyl group or
Y is a R-substituted benzyl group, or is (c) =CH—, and
Y is a R-substituted diphenylmethylidene group or (10,11-dihydro)-5H-dibenzo-[a,d]-cyclohepten-5-ylidene group,
R is H, alkyl, alkoxy, halogen and/or trihalogen methyl and the dotted line represents an optional bond, with the understanding that from the R-substituted phenyl rings one or more may be replaced by a R-substituted heterocyclic aromatic ring and their acid addition salts.

Possibly present R-substituted heterocyclic aromatic rings are for example: 2-, 3- and 4-pyridinyl, 4-imidazolyl, 4-thiazolyl, 2-guanidino-4-thiazolyl, 2- and 3-furanyl, 2-dimethylaminomethyl-5-furanyl, etc.

The results of pharmacological tests with said new compounds are summarized in Table A ($H_1$-activity) and Table B ($H_2$-activity). The values for the $H_1$-activity given are the mean of at least two experiments in quadruplicate, while the values for the $H_2$-activity result from at least two experiments in duplicate.

In Table A the tested compounds are defined by a formula, and the meaning of $R_1$ and n in the formula are stated in the table. In addition the compound have serial numbers corresponding with the serial numbers used in Table B. It is remarked that the last three compounds in the two tables do not fall within the invention, but are stated for comparison.

TABLE A

Histamine $H_1$-activity $$R_1-N(H)-C(=NH)-N(H)-(CH_2)_n-\text{imidazole}$$

| | $R_1$ | n | Ileum (pA2 0,2) | Trachea pA2 ± 0,2 |
|---|---|---|---|---|
| I | diphenylmethyl-S-propyl | 3 | 6,5 | 6,2 |
| II | diphenylmethyl-S-propyl | 2 | 6,4 | not determined |
| III | diphenylmethyl-O-propyl | 3 | 7,5 | 7,6 |

TABLE A-continued

Histamine H₁-activity $$R_1-\overset{H}{N}-\underset{\underset{NH}{\|}}{C}-\overset{H}{N}-(CH_2)_n-\text{[imidazole]}$$

| | R₁ | n | Ileum (pA₂ 0,2) | Trachea pA₂ ± 0,2 |
|---|---|---|---|---|
| IV | 4-methylphenyl-phenyl-CH-S-propyl | 3 | 6,4 | 6,5 |
| V | (same) | 2 | 6,6 | not determined |
| VI | 4-fluorophenyl-phenyl-CH-S-propyl | 3 | 6,6 | 6,8 |
| VII | 2-methylphenyl-(2-pyridyl)-CH-S-propyl | 3 | 6,4 | 6,0 |
| VIII | diphenyl-CH-CH₂-CH₂- | 2 | 6,2 | not determined |
| IX | (same) | 3 | 6,3 | not determined |
| X | 1,1-diphenyl-1-propenyl | 3 | 6,7 | 6,2 |
| XI | N-benzyl-N-phenyl-propyl | 3 | 7,6 | 7,8 |

TABLE A-continued

Histamine H₁-activity

|  | R₁ | n | Ileum (pA₂ 0,2) | Trachea pA₂ ± 0,2) |
|---|---|---|---|---|
| XII | 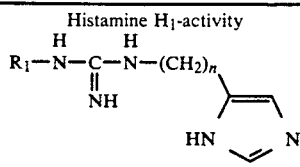 [3] | 3 | 5,5 | not determined |
| XIII | Impromidine |  | 5,5 | not determined |
| XIV | Diphenhydramine |  | 8,0 | not determined |

TABLE B

|  |  | Histamine H₂-activity | | | |
|---|---|---|---|---|---|
|  |  | atrium | | gastric fundus | |
|  |  | α | pD₂ (±0,1) | α | pD₂ (±0,2) |
| I |  | 1,0 | 6,8 | 1,0 | 6,1 |
| II |  | 0,8 | 4,8 | 0,5 | 4,9 |
| III |  | 0,9 | 5,5 | 0,4 | 5,8 |
| IV |  | 0,8 | 5,9 | not determined | |
| V |  | 0 | 4,0 | 0 | 4,0 |
| VI |  | 0,8 | 5,9 | 0,4 | 5,5 |
| VII |  | 0,8 | 5,9 | not determined | |
| VIII |  | 0,9 | 5,6 | 0 | 5,0 |
| IX |  | 1,0 | 7,7 | not determined | |
| X |  | 1,0 | 7,0 | 0,9 | 5,6 |
| XI |  | 1,0 | 6,4 | 0,7 | 6,5 |
| XII |  | 1,0 | 7,2 | 1,0 | 7,6 |
| XV | Histamine | 1,0 | 6,1 | 1,0 | 5,5 |
| XIII | Impromidine | 1,0 | 7,8 | 1,0 | 8,5 |

DISCUSSION

H₁-activity

There is no change in H₁-activity when changing the 5-methylimidazole part of impromidine in a phenyl group (compound XII). However, introducing an extra phenyl group in compound XII results in an increase in pA₂ from 5.5 to 6.5 (Compound I) on the guinea-pig ileum. Shortening the trimethylene chain in compound I to an ethylene chain (compound II) has no effect on the H₁-activity. Analogous results have been obtained when comparing compound IV with compound V and compound VIII with compound IX.

Substituting an oxygen for the sulphur atom (compound III) turned out to be ten times as potent as the starting compound on the guinea-pig ileum and even 25 times as potent on the trachea.

Introducing a paramethyl group (compounds IV and V) or a parafluoro group (compound VI) has only little or no effect at all on the H₁-antagonism.

Also compounds VII, VIII, IX and X are almost as potent H₁-antagonists as compound I. Compound XI seems to be even a slightly more potent H₁-antagonist than the oxygen analogue compound II.

H₂-activity

Replacing the 5-methylimidazole group of impromidine by a phenyl group (compound XII) is attended with a 4-fold decrease in H₂-activity on the guinea-pig atrium and an 8-fold decrease on the gastric fundus. Introduction of an extra phenyl group in compound XII (compound I) results in a 2 a 3 fold reduction in H₂-agonism on the atrium and even 32-fold decrease in H₂-agonism on the fundus.

Shortening the trimethylene chain of compound I to an ethylene chain (compound II) results in a marked decrease in H₂-activity, both on the atrium and on the fundus. Analogous results have been obtained with the compound IV with regard to compound V and the compound VIII with regard to compound IX.

Replacing the sulphur atom in compound I by an oxygen atom (compound III) results in a 20-fold decrease in H₂-agonism on the atrium. On the gastric fundus the change in pD₂ is less pronounced but in this test system this change in structure is attended with a remarkable decrease in intrinsic activity.

Also introduction of a para methyl group (compounds IV and V) or a para fluoro group (compound VI) results in a strong decrease in H₂-activity.

Compound VII was found to be an almost as potent H₂-antagonist as the para methyl and fluoro analogues.

When the sulphur atom in compounds I and II is omitted, the diphenylpropyl analogues, compounds VIII and IX are obtained. These compounds show a remarkable high potency on the guinea-pig right atrium. Compound IX was found to be almost as potent as impromidine on the atrium.

Introduction of a double bond (compound X) results in a 4-fold decrease in H₂-activity on the atrium. The amino analogue, compound XI, proved to be about twice as potent as histamine on the atrium and to have about 4% of the activity of impromidine in this test system. On the gastric fundus this compound has about 1% of the activity of impromidine and 10 times the activity of histamine.

Conclusions

The oxygen analogue, compound III, and the amino analogue, compound XI, turned out to be the most potent H₁-antagonists of this series of impromidine analogues.

Compounds I, IX and X proved to be the most potent compounds of this series on the guinea-pig right atrium.

Because of their combination of qualities compounds I, IX, X and XI are the most preferred compounds.

The pharmacological tests were carried out as follows:

Guinea-pig trachea ($H_1$)

Male guinea-pigs (350-500 g) were killed by a blow on the head and the trachea removed. Single segments were cut from the trachea, loaded with 0.4 g and placed in an organ bath (35° C.) containing 120 mM NaCl, 6 mM KCl, 1 mM $MgSO_4$, 2.5 mM $CaCl_2$, 1 mM $NaH_2PO_4$, 2.5 mM $NaHCO_3$ and 6 mM glucose. The organ bath was gassed with oxygen containing 5% $CO_2$. $PD_2$, intrinsic acitivity and antagonistic activity of the test compounds were determined from isotonically recorded, cumulative dose-response curves.

The $H_1$-specificity of the organ has been established by blocking the histamine induced contractions of the trachea with mepyramine. Moreover, both the specific histamine $H_2$-agonist dimaprit (up to $10^{-3}M$) and the specific histamine $H_2$-antagonist cimetidine (up to $10^{-4}M$) proved to have neither effect on the resting state of the organ nor on the histamine induced contractions.

Guinea-pig ileum ($H_1$)

Histamine $H_1$-activity at the guinea-pig ileum has been determined as described by Emmett et al. J. Med. Chem., 25, 1168-1174 (1982).

Guinea-pig right atrium $H_2$

Histamine $H_2$-activity at the guinea-pig right atrium has been determined as described by Sterk et al. Eur. J. Med.—Chim. Ther., 19, 545-550 (1984).

Guinea-pig gastric acid secretion ($H_2$)

Histamine $H_2$-activity at the acid secretion of the isolated gastric fundus of the guinea-pig has been determined as described by Impicciatore et al. Eur. J. Pharmacol., 48, 249-254 (1975).

Synthesis

The present compounds are prepared according to reaction scheme A or B. In these reaction schemes $R_x$ corresponds with the group $Y-X-(CH_2)_m-$ of formula 1.

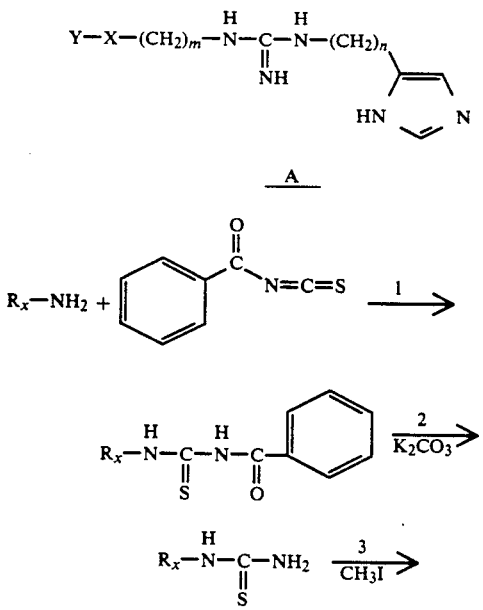

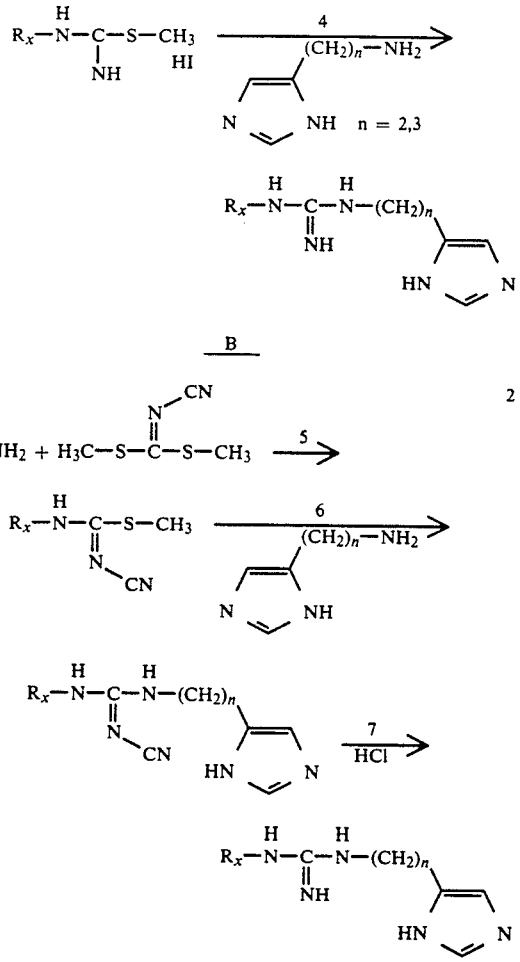

The primary amines used in step 1 and step 5, were prepared according to methods described in the literature or were commercially available (3.3-diphenyl propylamine).

The reaction of the primary amines with benzoylisothiocyanate to form the benzoyl thiourea derivatives (step 1) proceeded with high yields (66-88%). The hydrolysis of these benzoylthioureas derivatives (step 2) also proceeded with high yields (80-93%). The isothioureas resulting from the reaction of the thioureas with methyl iodide (step 3) were not isolated, but reacted directly, after evaporating the excess of methyl iodide, with 4-(3-aminopropyl)imidazole or 4-(2-aminoethyl)imidazole (step 4). The last reaction gave only poor yields (8-30%) no matter how long the reaction time (up to 140 hours refluxing in 1-propanol).

The compounds with a basic group in the '$R_x$part' (compounds VII and XI) were synthesized via their corresponding cyano-guanidine. The primary amines were first reacted with dimethyl-cyanoiminodithiocarbonate (step 5). This reaction proceeded very well and resulted in high yields of the isothioureas (about 70%). These N-cyanoisothioureas were reacted with 4-(3-aminopropyl) imidazole to form the cyanoguanidines (step 6). This reaction gave only very poor yields (10-20%). Also in this case no increase in yield could be observed when increasing the reaction time beyond 70 hours.

The hydrolysis of these cyanoguanidines to the end products (compounds VII and XI) gave an almost quantitative yield. These products were purified as their tripicrates in order to remove the ammoniumchloride formed in this hydrolysis.

SYNTHESIS OF THE AMINES

2-(diphenylmethylthio)ethylamine. HCl. ($A_1$)

This compound is prepared according to R. G. Hiskey and M. A. Harpold Tetrahedr., 23, 3923–3929 (1967).

2-(diphenylmethoxy)ethylamine.maleic acid ($A_2$)

This compound is prepared according to Van der Stelt et al. Arzneimitt.Forsch. 17, 1446–1449 (1967).

General process for the synthesis of 2-[alpha-phenyl-4-methylbenzylthio]ethylamine ($A_3$) and 2-[alpha-phenyl-4-fluorbenzylthio]ethylamine.HCl ($A_4$)

Compounds $A_3$ and $A_4$ are prepared analogous to the method mentioned for the preparation of compound $A_1$.

A solution of 0.2 mole of the desired substituted benzhydrol, 0.2 mole of cysteamine and 28 ml of borontrifluoride etherate in 200 ml of acetic acid was refluxed for one hour. After cooling the solution was evaporated and the residue crystallized from 2-propanol/ether.

Results:

$A_3$: the free base was distilled under reduced pressure, boiling point $_{0.1}$: 115°–120° C.

melting point of the dihydrogen maleate: 125°–128° C.

yield: 86%

$^1$H-NMR: (CDCl$_3$, free base): 1.32 ppm, singlet, 1.8 H; 2.28 ppm, singlet, 3.0H; 2.36–2.94 ppm, multiplet, 4.0 H; 5.12 ppm, singlet, 1.0H; 6.77–7.60 ppm, multiplet, 9.3 H.

$A_4$: melting point 144°–148° C.

yield: 92%

$^1$H-NMR (CDCl$_3$, free base): 1.28 ppm, singlet, 2.0H; 2.35–2.98 ppm, multiplet, 4.0 H; 5.12 ppm, singlet, 1.0 H; 6.76–7.54 ppm, multiplet, 9.2 H.

3.3-diphenylprop-2-enylamine, HCl ($A_5$)

This compound can be prepared according to Jones et al. J. Med. Chem., 14, 161–164 (1971).

3.3-diphenylpropylamine ($A_6$)

This compound is commercially available.

N-benzyl-N-phenylethylenediamine. HCl ($A_7$)

This compound is prepared according to U.S. Pat. No. 2,505,133.

General procedure for the preparation of the benzoylthioures derivatives ($B_1$–$B_6$)

A solution of about 20 g of the free base of the corresponding amine ($A_1$–$A_6$) in 100 ml of CHCl$_3$ was added slowly to a solution of an equimolar amount of benzoylisothiocyanate in 100 ml of CHCl$_3$. The resultant solution was refluxed for 15 minutes and subsequently concentrated under reduced pressure to approximately 50 ml. Addition of diethyl ether caused crystallisation. The precipitate was filtered off, washed with ether and dried.

N-benzoyl-N'-[2-(diphenylmethylthio)ethyl]thiourea ($B_1$)

Yield: 88% melting point: 101°–103° C.

$^1$H-NMR (CDCl$_3$): 2.70 ppm, triplet, J=6.0 Hz, 2.1 H; 3.78 ppm, quartet, J=6.0 Hz, 2.0 H; 5.26 ppm, singlet, 1.0 H; 7.04–7.96 ppm, multiplet, 16.0 H; 8.96 ppm, singlet (b), 0.9 H; 10.9 ppm, triplet (b), J=5.8 Hz, 0.9 H.

N-benzoyl-N'-[2-(diphenylmethoxy)ethyl]thiourea ($B_2$)

Yield: 87% melting point: 123°–125° C.

$^1$H-NMR (CDCl$_3$): 3.60 ppm, triplet, J=5.5 Hz, 2.0H; 3.90 ppm, quartet, J=5.4 Hz, 2.0 H; 5.34 ppm, singlet, 1.0 H; 7.02–7.88 ppm, multiplet, 15.0 H; 8.88 ppm, singlet (b), 0.9 H; 11.00 ppm, singlet (b), 0.9 H.

N-benzoyl-N'-2-[alpha-phenyl-4-methylbenzylthio]ethylthiourea ($B_3$)

Yield: 87% oil, purified by column chromotography (silica 0.063–0.200 mm, chloroform)

$^1$H-NMR (CDCl$_3$): 2.29 ppm, singlet, 3.0 H: 2.70 ppm, triplet, J=6.0 Hz, 2.0 H; 3.77 ppm, quartet, J=6.0 Hz, 2.0 H; 5.26 ppm, singlet, 1.0 H: 7.02–7.94 ppm, multiplet, 15.0 H; 8.94 ppm, singlet (b), 0.9 H; 10.2 ppm, triplet (b). J=5.6 Hz, 0.9 H.

N-benzoyl-N'-[2-(alpha-phenyl-4-fluorobenzylthio)ethyl]-thiourea ($B_4$)

Yield: 70% melting point: 99°–102° C.

$^1$H-NMR (CDCl$_3$): 2.70 ppm, triplet, J=5.9 Hz, 1.9 H; 3.84 ppm, quartet, J=5.9 Hz, 1.8 H; 5.29 ppm, singlet, 0.9 H; 6.74–7.93 ppm, multiplet 14.7 H; 8.97 ppm, singlet, 0.8 H; 10.88 ppm, triplet, J=5.9 Hz, 0.9 H.

N-benzoyl-N'-(3.3-diphenylprop-2-enyl)thiourea ($B_5$)

Yield: 85% melting point: 140°–141° C.

$^1$H-NMR (CDCl$_3$): 3.62–3.85 ppm, disturbed quartet, 1.7 H; 5.59 ppm, triplet, J=7.1 Hz, 0.9 H; 6.38–7.29 ppm, multiplet, 15.6 H; 8.31 ppm, singlet, 0.9 H; 10.08 ppm, singlet, 0.8 Hz.

N-benzoyl-N'-(3.3-diphenylpropyl)thiourea ($B_6$)

Yield: 66% melting point: 116°–118° C.

$^1$H-NMR (CDCl$_3$): 2.47 ppm, quartet, J=7.4 Hz, 1.8 H; 3.64 ppm, quartet, J=7.4 Hz, 1.8H; 4.02 ppm, triplet, J=7.4 Hz, 1.0 H; 7.00–7.96 ppm, multiplet, 15.7 H; 8.91 ppm, singlet, 0.8 H; 10.68 ppm, singlet, 0.8 H.

General procedure for the preparation of thioureas ($C_1$–$C_6$).

A solution of 25 g of a benzoylthiourea ($B_1B_6$) in a mixture of 200 ml acetone and 200 ml methanol was added slowly to a solution of 25 g K$_2$CO$_3$ in 200 ml H$_2$O at 80° C. The resultant mixture was refluxed for 2 hours. After concentrating the mixture under reduced pressure the thiourea analogue ($C_1$–$C_6$) crystallized.

N-[2-(diphenylmethylthio)ethyl]thiourea ($C_1$)

Yield: 86% melting point: 67°–70° C.

$^1$H-NMR (CDCl$_3$): 2.60 ppm, triplet, J=6.3 Hz, 2.0 H; 3.50 ppm, singlet (b), 2.0 H; 5.22 ppm, singlet, 1.0 H;

6.00 ppm, singlet, 2.0H; 6.90 ppm, triplet (b), J=6.0 Hz, 0.9 H; 7.14-7.56 ppm, multiplet, 10.0H.

N-[2-(diphenylmethoxy)ethyl]thiourea (C₂)

Yield: 87%
melting point: 128°-130° C.
¹H-NMR (CDCl₃): 3.08-3.90 ppm, multiplet (b), 4.0 H; 5.36 ppm, singlet, 1.0 H; 6.00-6.70 ppm, broad signal, 2.0 H; 7.30 ppm, singlet, 11.4 H.

N-[2-(alpha-phenyl-4-methylbenzylthio)ethyl]thiourea (C₃)

Yield: 85%
melting point: 115°-117° C.
¹H-NMR (DMSO-d₆): 2.29 ppm, singlet, 3.1 H; 2.58 ppm, triplet, J=5.4 Hz, 2.1H; 3.10-3.80 ppm, multiplet, 2.0H; 5.16 ppm, singlet, 1.0 H; 5.90 ppm, singlet, 1.8 H; 6.79 ppm, triplet, J=7.2 Hz, 1.0 H; 7.00-7.56 ppm, multiplet, 11.0 H.

N-[2-(alpha-phenyl-4-fluorobenzylthio)ethyl]thiourea (C₄)

Yield: 80%
melting point: 101°-105° C.
¹H-NMR (CDCl₃): 2.25 ppm, triplet, J=5.4 Hz, 2.0 H; 3.02-3.92 ppm, multiplet, 2.0 H; 5.22 ppm, singlet, 2.0 H: 6.11 ppm, singlet, 1.8 H; 6.76-7.53 ppm, multiplet, 10.4 H.

N-(3.3.diphenylprop-2-enyl)thiourea (C₅)

Yield: 81%
melting point: 201°-203° C.
¹H-NMR (DMSO-d₆): 3.81-4.19 ppm, multiplet, 2.1H; 6.12 ppm, triplet, J=6.3 Hz, 1.0H; 6.73-7.58 ppm, multiplet, 10.9H; 8.31 ppm, singlet, 2.1H.

N-(3.3-diphenylpropyl)thiourea (C₆)

Yield: 93%
melting point: 197°-199° C.
¹H-NMR (CDCl₃): 2.32 ppm, quartet, J=7.2 Hz, 2.0H; 3.13-3.60 ppm, multiplet, 2.0H; 4.00 ppm, triplet, J=7.2 Hz, 1.0H; 6.40 ppm, singlet, 2.0H; 6.94-7.60 ppm, multiplet, 11.4H.

N-[2-(N'-benzyl-N'-phenylamino)ethyl]-N''-cyano-S-methylisothiourea (C₇)

A solution of 15 g of N-benzyl-N-phenylethylenediamine in 100 ml of ether was added slowly to a stirred solution of N-cyanodimethyliminodithiocarbonate in 100 ml of ether. The resulting solution was stirred for 2 hours, after which the precipitate was filtered off, washed with either and dried.
Yield: 70%
melting point: 148°-152° C.
¹H-NMR (CDCl₃): 2.33 ppm, singlet, 2.6H; 3.30-3.76 ppm, multiplet, 4.1H; 4.55 ppm, singlet, 1.8H; 6.59-6.95 ppm, multiplet, 3.4H; 7.10-7.50 ppm, multiplet, 7.3H.

N-cyano-S-methyl-N'-(2-[2-methyl-alpha-(2-pyridyl)-benzylthio]ethyl) isothiourea (C₈)

A solution of 20 mg of 2 methylphenyl-2-pyridylmethanol and 11.4 g of cysteamine in 300 ml 48% HBr was refluxed for 5 hours and subsequently evaporated. The residue was dissolved in H₂O, brought at pH 11 with KOH, after which the aqueous phase was extracted with CHCl₃. The CHCl₃-layer was dried over MgSO₄ and evaporated. The residue was dissolved in ether and added slowly to a solution of 15 g of N-cyanodimethyliminodithiocarbonate. After stirring for 3 hours, the precipitate was filtered off, washed with ether and dried.
Yield: 60%
melting point: 96°-99° C.
¹H-NMR (CDCl₃): 2.34 ppm, singlet, 2.9H; (2.56 ppm, singlet; 2.71 ppm, triplet, J=6.3 Hz) together: 5.1H; 3.51 ppm, quartet, J=6.3 Hz, 2.0H; 5.47 ppm, singlet, 1.0H; 7.01-7.75 ppm, multiplet, 8.2H; 8.47-8.64 ppm, multiplet, 0.9H.

General procedure for the synthesis of the guanidines of examples I-VI and VIII-X.

A solution of 10 g of a thiourea (C₁-C₆) and 1.2 equivalents of methyl iodide in 200 ml of methanol was stirred for 18 hours at room temperature. After evaporating the solvent, a solution of 2.5 g of 4-(3-aminopropyl)imidazole or 4-(2-aminoethyl)imidazole in 200 ml of ethanol was added to the residue. The resultant mixture was refluxed for 70 hours and the product was purified by columnchromatography (silica gel 0.063-0.200 mm).

General procedure for the synthesis of the guanidine derivatives of examples VII and XI.

A solution of 12 g of the appropriate S-methylisothiourea derivative (C₇ or C₈) and 2.5 g of 4-(3-aminopropyl)imidazole in 300 ml ethanol was refluxed for 70 hours. After evaporating the solvent the residue was applied to a silica column and eluted with 50% mixture of ethanol and chloroform. The fractions containing pure nitrile, were collected, the solvent was evaporated and the residue dissolved in 2N HCl. After refluxing for 3 hours the reaction mixture was evaporated and the residue dissolved in methanol and added to a solution of picric acid in methanol. The precipitated oil was washed thoroughly with methanol and dried in vacuo on which the oil solidified.

EXAMPLE I

N-[2-(diphenylmethylthio)ethyl]-N'-[3-(imidazol-4-yl)propyl] guanidine dihydrogenmaleate Elution with ethanol. The compound was crystallized in the presence of an excess of maleic acid from ethanol/ether.
Yield: 12%
melting point: 119°-123° C.
¹H-NMR (DMSO-d₆): 1.82 ppm, quintet, J=7.2 Hz, 2.0H; 2.38-2.82 ppm, multiplet, (+DMSO-d₅), 6.0H; 3.01-3.50 ppm, multiplet, 4.0H: 5.42 ppm, singlet, 1.0H; 6.06 ppm, singlet, 4.0H; 7.08-7.72 ppm, multiplet, 15.5H; 8.85 ppm, doublet, J=0.8 Hz, 0.9H.

EXAMPLE II

N-[2-(diphenylmethylthio)ethyl]-N'-[2-imidazol-4-yl)ethyl guanidine dihydrogenmaleate Elution with a 50% mixture of ethyl acetate and ethanol. The compound was crystallized in the presence of an excess of maleic acid from ethanol/ether.
Yield: 22%
melting point: 152°-155° C.
¹H-NMR (DMSO-d₆): 2.52 ppm, triplet. J=5.9 Hz, (+DMSO-d₅), 3.0H: 3.86 ppm, triplet, J=5.9 Hz, 2.0H; 3.10-3.64 ppm, multiplet, 4.0H; 5.41 ppm, singlet, 1.0H; 6.09 ppm, singlet, 4.0H; 7.16-7.72 ppm, multiplet, 15.4H; 8.74 ppm, singlet 1.0H.

EXAMPLE III

N-[2-(diphenylmethoxy)ethyl]-N'-[3-(imidazol-4-yl)propyl] guanidine. 3/2 dihydrogenmaleate Elution with propanol-2 and crystallized in the presence of an excess of maleic acid from methanol/ether.
Yield: 8%
melting point: 132°–135° C.
$^1$H-NMR (DMSO-$d_6$): 1.74 ppm, quintet, J=7.2 Hz, 2.0H; 2.60 ppm, triplet (+DMSO-$d_5$), J=7.2 Hz, 2.1H; 3.00–3.60 ppm, multiplet (+$H_2O$) 6.0H; 5.46 ppm, singlet, 1.0H; 6.02 ppm, singlet, 3.0H; 7.06–7.62 ppm, multiplet, 14.0H; 8.76 ppm, singlet, 0.9H.

EXAMPLE IV

N-[3-(imidazol-4-yl)propyl]-N'-2-[α-phenyl-4-methylbenzylthio]ethyl guanidine dipicrate Elution with a 50% mixture of ethyl acetate and ethanol. The product was crystallized in the presence of an excess of picric acid from methanol/$H_2O$.
Yield: 18%
melting point: 76°–78° C.
$^1$H-NMR (DMSO-$d_6$): 1.78 ppm, quintet, 2.0H; 2.22 ppm, singlet, 3.0H; 2.31–2.74 ppm, multiplet, 11.0H(+DMSO-$d_5$); 3.00–3.73 ppm, multiplet, 12.0H ($H_2O$); 5.28 ppm, singlet, 1.0H; 6.90–7.53 ppm, multiplet, 11.4H; 8.52 ppm, singlet, 4.0H; 8.92 ppm, singlet, 1.2H; 14.00 ppm, singlet, 2.0H.

EXAMPLE V

4-[2-(imidazol-4-yl)ethyl]-N'-2-[α-phenyl-4-methylbenzylthio]ethyl guanidine. dihydrogen/maleate Elution with a 50% mixture of ethylacetate and propanol-2. The product was crystallized in the presence of an excess of maleic acid from propanol-2/ethylacetate.
Yield: 32%
melting point: 119°–121° C.
$^1$H-NMR (DMSO-$d_6$): 2.24 ppm, singlet, 2.8H; 2.32–2.65 ppm, multiplet, 9.1H (+DMSO-$d_5$); 2.80 ppm, triplet, J=6.3 Hz, 2.0H; 3.14–3.62 ppm, multiplet, 3.8H; 5.33 ppm, singlet, 1.0H; 6.05 ppm, singlet, 4.0H; 7.00–7.62 ppm, multiplet, 14.8H; 8.63 ppm, singlet, 1 OH.

EXAMPLE VI

N-[2-(α-phenyl-4-fluorobenzylthio)ethyl]-N'-[3-(imidazol-4-yl) propyl]guanidine. dihydrogenoxalate Elution with a 50% mixture of ethylacetate and propanol-2. The compound was crystallized in the presence of an excess of oxalic acid from methanol/ethylacetate.
Yield: 15%
melting point: 83°–85° C.
$^1$H-NMR: (dipicrate; DMSO-$d_6$) 1.70–1.96 ppm, quintet, J=6.9 Hz, 1.9H; 2.34–2.90 ppm, multiplet, (+DMSO-$d_5$), 5.1H; 3.00–3.53 ppm, multiplet, 4.0H; 5.43 ppm, singlet, 1.0H; 7.00–7.87 ppm, multiplet, 15.4H; 8.60 ppm, singlet, 3.9H; 9.03 ppm, doublet, J=0.8 Hz, 0.8H; 14.05 ppm. singlet (b) 2.1H.

EXAMPLE VII

N-[3-(imidazol-4-yl)propyl]-N'-(2-[2-methyl-alpha-(2-pyridyl) benzylthio]ethyl)guanidine. tripicrate Yield: 5%
melting point: 98°–102° C.
$^1$H-NMR (DMSO-$d_6$): 1.82 ppm, quintet, J=7.0 Hz, 2.0H; 2.38 ppm, singlet, 3.0H; 2.45–2.83 ppm, multiplet, (+DMSO-$d_5$), 7.8H; 3.02–3.60 ppm, multiplet, 4.0H; 5.68 ppm, singlet, 1.0H; 7.08–8.83 ppm, multiplet, 19.0H; 9.03 ppm, singlet, 1.0H; 14.02 ppm, singlet (b), 2.0H.

EXAMPLE VIII

N-(3.3-diphenylpropyl)-N'-[2-(imidazol-4-yl)ethyl] guanidine. dihydrogen maleate.

Elution with a 50% mixture of ethylacetate and ethanol. The product was crystallized in the presence of an excess of maleic acid from propanol-2/ethylacetate.
Yield: 32%
melting point: 115°–118° C.
$^1$H-NMR ($D_2O$): 2.33 ppm, quartet, J=7.3 Hz, 2.0H; 2.94 ppm, triplet, J=7.1 Hz, 2.0H; 3.16 ppm, triplet, J=7.1 Hz, 2.0H; 3.41 ppm, triplet, J=7.1 Hz, 2.0H; 4.03 ppm, triplet, J=7.3 Hz, 1.0H; 6.34 ppm, singlet, 4.3H; 7.15–7.44 ppm, multiplet, 10.5H; 8.56 ppm, doublet, J=1.2 Hz, 0.8H.

EXAMPLE IX

N-(3.3-diphenylpropyl)-N'-[3-(imidazol-4-yl)propyl]-guanidine. dipicrate

Elution with a 50% mixture of ethylacetate and ethanol. The product was crystallized in the presence of an excess of picric acid from propanol-2/ether.
Yield: 12%
melting point: 73°–77° C.
$^1$H-NMR (DMSO-$d_6$): 1.78 ppm, quintet, J=7.5 Hz, 2.0H; (2.32 ppm, triplet, J=7.5 Hz; 2.68 ppm, triplet, J=7.5 Hz) together (+DMSO-$d_5$) 8.3H; 2.87–3.30 ppm, multiplet, 4.0H; 4.00 ppm, triplet, J=7.5 Hz, 1.0H; (7.28 ppm, singlet: 7.43 ppm, singlet) together 16.2H; 8.60 ppm, singlet, 4.0H; 9.00 ppm, doublet, J=0.8 Hz, 1.0H; 14.13 ppm, singlet (b). 2.0H.

EXAMPLE X

N-(3.3-diphenylprop-2-enyl)-N'-[3-imidazol-4-yl)propyl] guanidine. H1

Crystallized from ethanol/diethylether.
Yield: 10%
melting point: 73°–76° C.
$^1$H-NMR (DMSO-$d_5$): 1.80 ppm, quintet, J=7.0 Hz, 2.0H; 2.39–2.80 ppm, multiplet, (+DMSO-$d_5$) 4.1H; 2.94–3.37 ppm, multiplet, 2.0H; 2.84 ppm, triplet, J=7.0 Jz, 2.0H; 6.13 ppm, triplet, J=7.0 Hz, 1.0H; 7.00–8.20 ppm. multiplet, 16.5H: 8.35 ppm, singlet, 1.0H.

EXAMPLE XI

N-[2-(N'-benzyl-N'-phenylamino)ethyl]-N''-[3-(imidazol-4-yl) propyl]guanidine, tripicrate Yield: 6%
$^1$H-NMR (DMSO-$d_6$): 1.80 ppm, quintet, J=7.0 Hz, 2.0H; 2.42–2.85 ppm, multiplet, (+DMSO-$d_5$) 4.4H+2.97–377 ppm, multiplet (+$H_2O$) 6.6H; 4.62 ppm, singlet, 2.0H; 6.41–7.74 ppm, multiplet, 17.0H; 8.64 ppm, singlet, 6.0H; 9.03 ppm, singlet, 1.0H; 14.20 ppm, singlet (b), 2.0H.

We claim:
1. N-(w-substituted alkyl)-N'-[(imidazole-4-yl)alkyl]-guanidine of the formula:

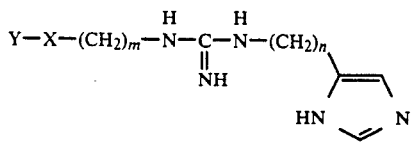

wherein m is 1,2 or 3;

n is 2 or 3;

X is (a) $CH_2$, and Y is an R substituted diphenylmethyl group, or X is:

(b) =CH—, and Y is an R-substituted diphenylmethylidene group,

R is a member selected from the group consisting of alkyl, alkoxy, halogen and trihalogen methyl, and the dotted line represents an optional bond, and the acid addition salts thereof.

2. Compound according to claim 1, wherein n=3.

3. Compound according to claim 1, wherein m is 2.

4. Compound according to claim 1, wherein X is =CH—.

5. Compound according to claim 1, wherein R is hydrogen.

6. Pharmaceutical composition for the treatment of congestive heart failures and some allergic conditions, wherein the composition comprises at least one compound of the formula

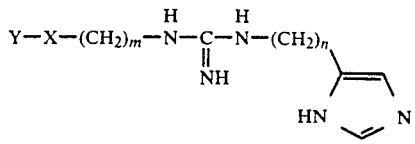

as defined in claim 1 or an acid addition salt thereof, as an active substance and a carrier.

7. N-(3,3-diphenylprop-2-enyl)-N'-[3-(imidazole-4-yl)propyl]guanidine.

8. A method for treating an allergic condition which comprises administering a therapeutically effective amount of the pharmaceutical composition of claim 6.

9. A method for treating congestive heart failure which comprises administering a therapeutically effective amount of a pharmaceutical composition comprised of an N-(w-substituted alkyl)-N'-[(imidazole-4-yl)alkyl]-guanidine of the formula:

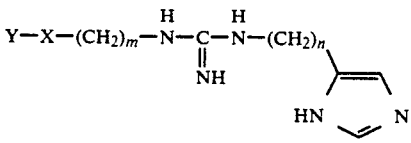

wherein m is 1, 2 or 3;

n is 2 or 3;

X is:

(a) $CH_2$, and Y is an R substituted diphenylmethyl group, or X is:

(b) =CH—, and Y is an R-substituted diphenylmethylidene group,

R is a member selected from the group consisting of H, alkyl, alkoxy, halogen and trihalogen methyl, and the dotted line represents an optional bond, and the acid addition salts thereof, and a pharmaceutically acceptable carrier.

* * * * *